United States Patent [19]

Gebel et al.

[11] Patent Number: 4,727,858
[45] Date of Patent: Mar. 1, 1988

[54] HIGH INTENSITY SELECTABLE POLY OR MONOCHROMATIC SLIT LIGHT SOURCE APPARATUS FOR OPTICAL INSTRUMENTS

[75] Inventors: Radames K. H. Gebel, Fairborn; Thomas R. Connon; Willi J. Buehring, both of Dayton; Gregory R. Bothe, West Carrollton, all of Ohio

[73] Assignee: The United States of America as represented by the Secretary of the Air Force, Washington, D.C.

[21] Appl. No.: 883,222

[22] Filed: Jul. 8, 1986

[51] Int. Cl.[4] .............................................. A61B 1/06
[52] U.S. Cl. ......................................................... 128/6
[58] Field of Search .................. 351/221; 128/4, 6, 3, 128/5, 7, 23

[56] References Cited

U.S. PATENT DOCUMENTS

| | | | |
|---|---|---|---|
| 1,751,584 | 3/1930 | Hansell | 128/4 X |
| 3,583,795 | 6/1971 | Heine | 351/221 |
| 3,597,051 | 8/1971 | Copeland | 351/221 |
| 3,699,950 | 10/1972 | Humphrey, Jr. et al. | 128/23 |
| 4,170,997 | 10/1979 | Pinnow et al. | 128/4 X |
| 4,597,030 | 6/1986 | Brody et al. | 128/23 X |

*Primary Examiner*—William H. Grieb
*Attorney, Agent, or Firm*—Fredric L. Sinder; Donald J. Singer

[57] ABSTRACT

An optical fiber apparatus is disclosed for providing light to optical and other instruments from an auxiliary light source which may include a laser. A disclosed embodiment comprises a retinascope with a light source optically connected to a fiber optic bundle having its individual fibers aligned in the shape of a circle at its input end and in the shape of a rectangle at its output end. Ferrules hold and align the fibers at both ends. The light source may be a pulsed or continuous wave laser producing substantially monochromatic light, or any other suitable poly- or monochromatic light source. The retinascope includes a holder for supporting the output ferrule and the fiber bundle output. The holder provides for adjusting both the linear and rotational position of the fiber optic bundle output end in relation to the retinascope head by including a cylindrical holder having an H-shaped slot through its side, a first sleeve surrounding the cylindrical holder, a headed set screw extending through a hold in the side of the first sleeve, then through the H-shaped slot, then through a threaded hold in an inner second sleeve, and finally against the output ferrule to hold the optical fiber output end in fixed alignment with the inner and outer sleeves. The retinascope may include a filter holder.

2 Claims, 8 Drawing Figures

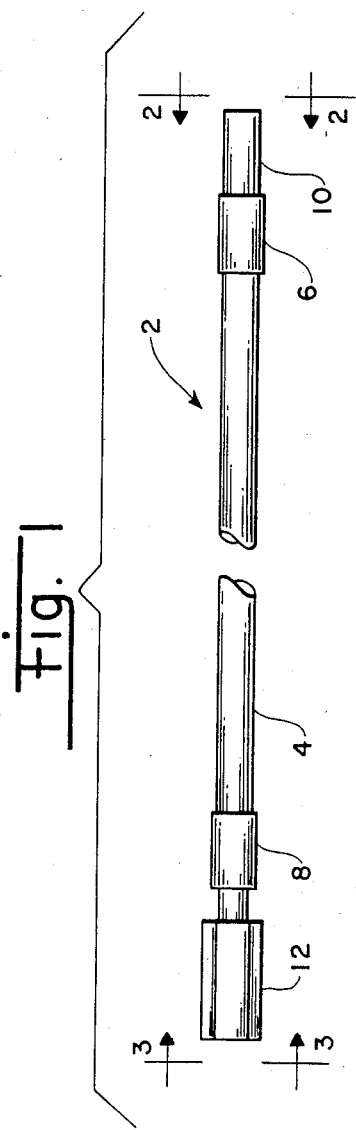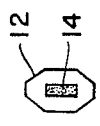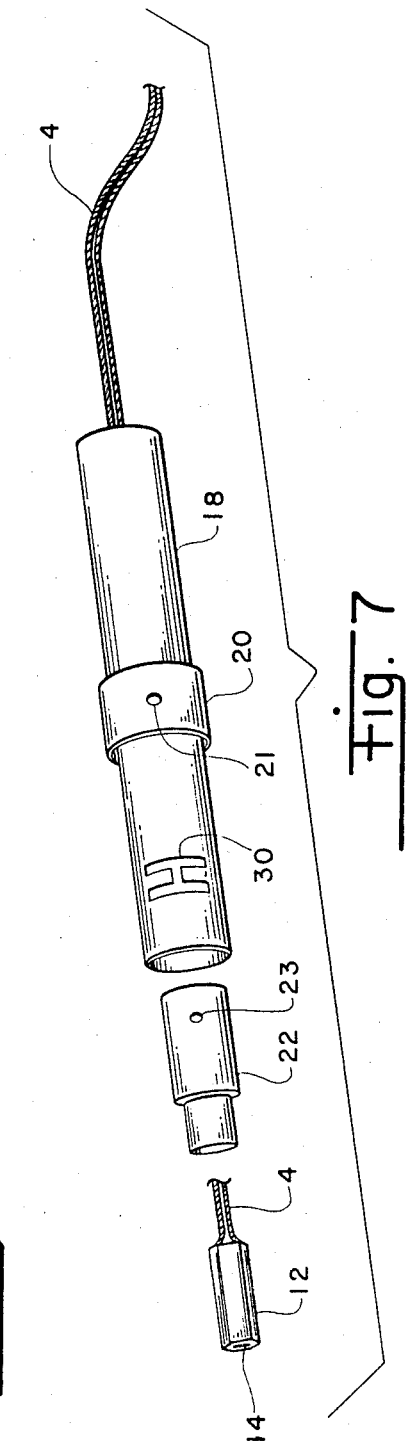

HIGH INTENSITY SELECTABLE POLY OR MONOCHROMATIC SLIT LIGHT SOURCE APPARATUS FOR OPTICAL INSTRUMENTS

RIGHTS OF THE GOVERNMENT

The invention described herein may be manufactured and used by or for the Government of the United States for all governmental purposes without the payment of any royalty.

BACKGROUND OF THE INVENTION

The present invention relates generally to optical and other instruments requiring light sources, and more specifically to an optical fiber apparatus that replaces an incandescent light bulb with an auxiliary light source which may include a laser.

Optical and other instruments frequently use incandescent light bulbs as a source of light. For example, many ophthalmic instruments, such as a retinascope, incorporate a slit lamp to project a thin bar-shaped beam of light upon an eye. Typical slit lamps use a small incandescent bulb as the light source. Such incandescent bulbs are limited in the amount of light they can produce by the temperature to which their filaments can be heated before melting or otherwise greatly reducing their useful operating life. These bulb filaments typically operate at a compromise temperature of about 2.860° K, producing a light spectrum with a visible peak in the red, but not strong enough in intensity for many ophthalmic investigations preferably done with red light. The desired bar-shape of the light beam is generally formed by projecting the light through a mechanical slit, which reduces the available total amount of light.

While present slit lamps are successfully used for many eye examinations, their light intensity usually is wanting for examining eyes made opaque from cataracts, the use of cholonergic glaucoma medication, or from other causes.

U.S. Pat. No. 3,068,745 to Peck describes a slit lamp for projecting a beam of light with very well defined edges. Peck optically connects a fiber optic bundle to an intense source of white light. Each individual fiber in the bundle is tapered from a wide end at the light source to a thin end at optics in front of an output light slit. An input light slit in front of the wide ends of the fibers shapes the light beam before it enters the optical fiber bundle. The progressive taper of the individual fibers produces a smaller bar-shaped light beam at the output end of the fiber bundle, but with much more sharply defined edges. While Peck's use of an optical fiber bundle allows the use of a brighter lamp than in typical slit lamps, much of the available light is lost by the light blocking effect of the input and output light slits. It is thus seen that there is a need for a more efficient solution which yields highly intense light for use as a source in ophthalmic and other instruments.

It is, therefore, a principal object of the present invention to provide light with a higher intensity than yielded by conventional straight-forward optical instrument light sources.

It is another object of the present invention to furnish light of high intensity in a versatile retinascope whereby convenient, one-handed operation, including focusing and rotation of the slit projection from the light source, still is maintained.

SUMMARY OF THE INVENTION

The present invention furnishes light to optical instruments that satisfies the aforementioned needs. Underlying the present invention is the recognition that one of the limitations of prior art optical instrument light sources is that the mechanical and optical beam aiming and shaping mechanisms greatly reduce the effective light from a light source. The slits in slit lamps block out much of the light from the lamp which thus is not utilized. Additionally, the low color temperatures of incandescent light bulbs with their spectral fade out in the blue restricts many optical investigations. Before the present invention, little consideration was apparently given to making the most efficient use of the available light in certain optical instruments, such as retinascopes.

The unique application of the present invention is that the light directing property of optical fibers is used to maximize the proportion of available light actually delivered as part of a preselected shaped beam. This, combined with the ability to select a preferred light color by the use of an appropriate laser as the light source, or narrow filters with other bright light sources, discloses an apparatus that provides a highly intense beam of light suitable for a variety of optical instruments, such as a retinascope, and is an improvement over conventional straight-forward use of incandescent lamps in most applications.

The described apparatus allows an incandescent light bulb, with its inherent limitations, to be replaced by a high intensity laser, or other suitable light source. This solution yields a large multiple of intensity over that which can be obtained from an incandescent light bulb modified by spectral filters.

Accordingly, the present invention is directed to an apparatus for providing light from a light source to an optical or other instrument, comprising a fiber optic bundle which has an input end optically connected to the light source, and a ferrule surrounding the output end to align all the optical fibers into a preselected shape.

The invention further includes the ferrule having a substantially rectangular opening. A filter may be placed between the light source and the input end.

The invention also includes a retinascope incorporating a modification of the light source apparatus. The retinascope includes a holder, or supporting means, which supports means for aligning all the optical fibers in a desired rectangular, or slit, shape. The holder may include means for adjusting both the linear and rotational position of the fiber optic bundle output end in relation to the retinascope head. The adjusting means may include a cylindrical holder having an H-shaped slot through its side, a first sleeve surrounding the cylindrical holder, a set screw extending through a hole in the side of the first sleeve, then through the H-shaped slot, then through a threaded hole in an inner second sleeve, and finally against the aligning means for the fiber optic output end to hold the output end in fixed alignment with the inner and outer sleeves. The retinascope may additionally include a filter placed between the light source and the input end.

DESCRIPTION OF THE DRAWINGS

The present invention will be more clearly understood from a reading of the following detailed description in conjunction with the accompanying drawings wherein:

FIG. 1 is a plan view of a fiber optic bundle incorporating the teachings of the present invention.

FIG. 2 is a view along line 2—2 of FIG. 1 of the circular input end of the fiber optic bundle.

FIG. 3 is a view along line 3—3 of FIG. 1 of the rectangular output end of the fiber optic bundle.

FIG. 7 is an exploded perspective view of a retinascope holder showing the interrelationship of the alignment slots, outer and inner alignment sleeves, and output ferrule.

DETAILED DESCRIPTION

Figure 4:
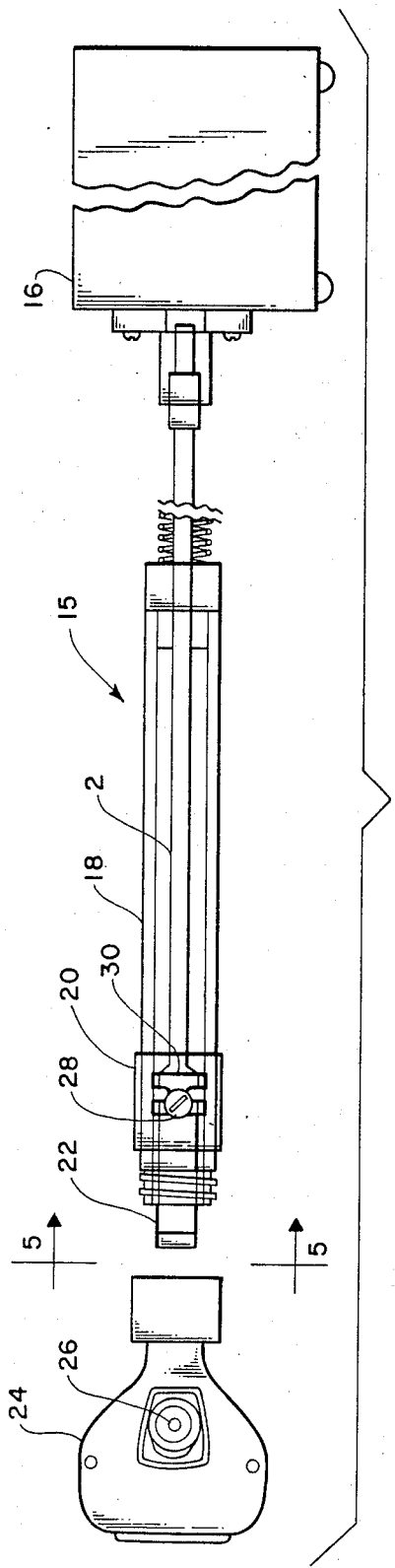
FIG. 4 is a plan view of a retinascope incorporating the teachings of the present invention.

Referring now to FIG. 1 of the drawings, there is shown a plan view of a fiber optic bundle assembly 2 incorporating the teachings of the present invention. The bundle assembly 2 comprises a plurality of individual optical fibers surrounded by a casing, typically comprising a PVC jacket 4 with cylindrical end caps 6 and 8 to secure the PVC jacket 4 to the fiber optic bundle. The bundle assembly 2 also includes two ferrules 10 and 12 to hold the individual fiber ends in shaped alignment. FIG. 2 is a view taken along line 2—2 of FIG. 1 of the circular input end of the fiber optic bundle, showing the ends of the individual fibers 14. FIG. 3 is a view taken along line 3—3 of FIG. 1 of the rectangular output end of the fiber optic bundle. Output ferrule 12 realigns all the fibers 14 present at the circular input end into a rectangular or slit shape for output. The entire bundle assembly 2 is approximately five feet in length and bends and flexes to allow convenient positioning of the output end of the fiber optic bundle assembly 2. The individual optical fibers should be as thin as possible for both flexibility and easier shaping of the output end. Fiber thicknesses of about 25 micrometers to about 50 micrometers are very suitable.

Figure 5:
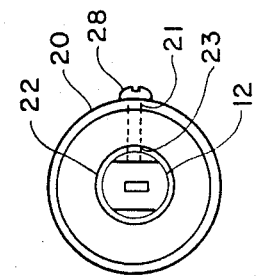
FIG. 5 is a view along line 5—5 of FIG. 4 showing the output end of the fiber optic bundle where it attaches to a retinascope head.

FIG. 4 is a plan view of a retinascope 15 incorporating the fiber optic bundle assembly 2. The primary components of the retinascope are a monochromatic laser light source 16, the fiber optic bundle assembly 2, cylindrical holder 18, outer alignment sleeve 20, brass inner alignment sleeve 22, and retinascope head 24. The retinascope head 24 is an off-the-shelf item, comprising internal optics (not shown) and a viewing lens 26 located on one side. The laser light source 16 is a Helium-Neon laser producing monochromatic red light at about a 623.8 nm wavelength. Outer 20 and inner 22 alignment sleeves include a set screw 28, which fits through a hole 21 in the side of outer sleeve 20, then through an H-shaped slot 30 (shown in boldline for emphasis) cut into cylindrical holder 18, and then through a threaded hole 23 in inner sleeve 22 to press against and hold in place output ferrule 12 as shown in FIG. 5, a view taken along line 5—5 of FIG. 4. A better understanding of the relationship among holder 18, H-shaped slot 30, and the outer 20 and inner 22 alignment sleeves will be obtained by examination of FIG. 7, an exploded view of those elements. The elements of FIG. 7 are shown axially displaced from their assembled positions for clarity.

The disclosed retinascope provides convenient one-handed use. The laser light source 16 may sit upon a table or the floor out of the way of the user. Rotation and focusing of the slit lamp is performed simply by turning outer alignment sleeve 20 with the thumb and forefinger of the hand holding the retinascope. The H-shaped slot 30 allows rotational movement of the slit output by movement of the setscrew 28 through the vertical slots of the "H", and focusing by movement of the setscrew 28 through the horizontal slot of the "H".

Figure 8:
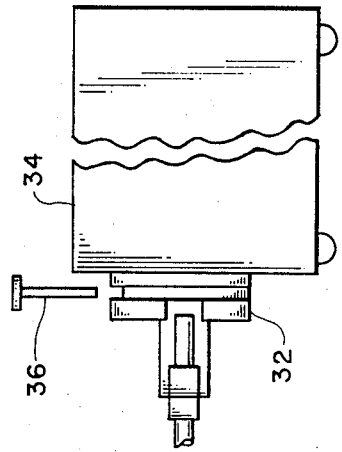
FIG. 8 is a plan view of a light source for a retinascope showing a filter and filter holder.
Figure 6:
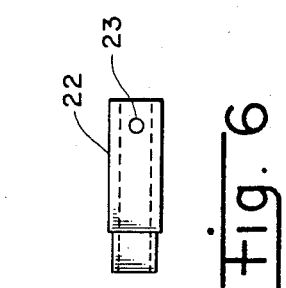
FIG. 6 is a plan view of a brass sleeve for positioning and orienting the output of the fiber optic bundle for focusing and rotational alignment.

FIG. 8 shows the addition of a filter holder 32 to a non-monochromatic light source 34 for receiving various filters 36. By choosing different narrow bandwidth filters, the detail contrast of the illuminated area may be increased. The use of filters is facilitated by using a circularly shaped input end for the fiber optic bundle. Detail contrast may similarly be increased by using monochromatic light sources of different wavelengths.

While the disclosed apparatus shows a continuous light source, for photographic and other similar uses a pulsed laser or other high intensity light source may be used. When using a pulsed light source, the camera shutter is synchronized with the pulsed light. Other high intensity light sources may include xenon discharge lamps, either continuous or pulsed.

It will be seen by those with skill in the art that the disclosed apparatus allows the convenient and efficient use of a variety of different light sources and is a substantial improvement over the straightforward use of incandescent bulbs and their accompaning complicated mechanical and optical beam directing and shaping mechanisms.

While the apparatus herein described constitutes a preferred embodiment of the invention, it is to be understood that the invention is not limited to this precise form of apparatus or method, and that changes may be made therein without departing from the scope of the invention as defined in the claims.

We claim:

1. A retinascope, comprising:
    (a) a light source;
    (b) a fiber optic bundle having an input end and an output end, the input end optically connected to the light source;
    (c) means for aligning all the optical fibers at the output end substantially in the shape of a rectangle;
    (d) means for supporting the aligning means;
    (e) a retinascope head attached to the supporting means; and,
    (f) wherein the supporting means includes:
        (i) means for adjusting the linear position of the fiber optic bundle output end in relation to the retinascope head; and,
        (ii) means for adjusting the rotational orientation of the fiber optic bundle output end in relation to the retinascope head.

2. The retinascope according to claim 1, wherein the linear position adjusting means and the rotational orientation adjusting means together comprise:
    (a) a cylindrical holder having a substantially H-shaped slot through its side;
    (b) a first sleeve positioned around the cylindrical holder and having a first hole through its side;
    (c) a setscrew having a shank having threads, the set screw shank extending through the first sleeve side hole and through the H-shaped slot; and,
    (d) a second sleeve positioned inside the cylindrical holder and having a threaded second hole through its side adapted for receipt of the set screw shank, the threaded second hole positioned above the aligning means for the fiber optic bundle output end so that the set screw, when tightened against the aligning means, holds the fiber optic bundle output end in fixed alignment with the first and second sleeves.

* * * * *